US012564608B2

(12) United States Patent
Lötvall et al.

(10) Patent No.: US 12,564,608 B2
(45) Date of Patent: Mar. 3, 2026

(54) USE OF GHOST NANOVESICLES AS THERAPEUTICS

(71) Applicant: Exocure Sweden AB, Gothenburg (SE)

(72) Inventors: Jan Lötvall, Lysekil (SE); Kyong-su Park, Gothenburg (SE)

(73) Assignee: Exocure Sweden AB, Goeteborg (SE)

( * ) Notice: Subject to any disclaimer, the term of this patent is extended or adjusted under 35 U.S.C. 154(b) by 955 days.

(21) Appl. No.: 17/642,140

(22) PCT Filed: Sep. 11, 2020

(86) PCT No.: PCT/US2020/050535
§ 371 (c)(1),
(2) Date: Mar. 10, 2022

(87) PCT Pub. No.: WO2021/050975
PCT Pub. Date: Mar. 18, 2021

(65) Prior Publication Data
US 2022/0387505 A1     Dec. 8, 2022

Related U.S. Application Data

(60) Provisional application No. 62/899,931, filed on Sep. 13, 2019.

(51) Int. Cl.
| | |
|---|---|
| *A61K 35/28* | (2015.01) |
| *A61K 9/00* | (2006.01) |
| *A61K 38/19* | (2006.01) |
| *A61K 38/20* | (2006.01) |
| *A61P 29/00* | (2006.01) |
| *A61K 39/00* | (2006.01) |

(52) U.S. Cl.
CPC ............ *A61K 35/28* (2013.01); *A61K 9/0019* (2013.01); *A61K 38/191* (2013.01); *A61K 38/20* (2013.01); *A61P 29/00* (2018.01); *A61K 39/00* (2013.01)

(58) Field of Classification Search
CPC .... A61K 35/28; A61K 9/0019; A61K 38/191; A61K 38/20; A61K 39/00; A61P 29/00
See application file for complete search history.

(56) References Cited

U.S. PATENT DOCUMENTS

| | | | |
|---|---|---|---|
| 9,149,542 | B2 | 10/2015 | Gho et al. |
| 9,220,763 | B2 | 12/2015 | Gho et al. |
| 11,333,665 | B2 | 5/2022 | Lotvall et al. |
| 2008/0207723 | A1 | 8/2008 | Kopreski |
| 2015/0086639 | A1 | 3/2015 | Huang |
| 2015/0218254 | A1 | 8/2015 | Sabbadini et al. |
| 2016/0061842 | A1 | 3/2016 | Di Vizio |
| 2016/0120818 | A1 | 5/2016 | Grandi et al. |
| 2018/0036240 | A1 | 2/2018 | Gho et al. |
| 2018/0296483 | A1 | 10/2018 | Gho et al. |
| 2018/0318409 | A1 | 11/2018 | Valiante et al. |
| 2020/0249234 | A1 | 8/2020 | Lotvall et al. |
| 2022/0080035 | A1 | 3/2022 | Park et al. |

FOREIGN PATENT DOCUMENTS

| | | | |
|---|---|---|---|
| EP | 2617413 A2 | 7/2013 | |
| EP | 3251659 A1 | 12/2017 | |
| EP | 2450032 B1 | 9/2018 | |
| WO | WO2009051427 | 4/2009 | |
| WO | WO2009130649 | 10/2009 | |
| WO | WO2010010983 | 1/2010 | |
| WO | WO2010056337 | 5/2010 | |
| WO | WO2010070124 | 6/2010 | |
| WO | WO2013063439 | 5/2013 | |
| WO | WO2015085096 | 6/2015 | |
| WO | WO2016136372 | 9/2016 | |
| WO | WO2017161010 | 9/2017 | |
| WO | WO2017205810 | 11/2017 | |
| WO | WO2018171947 | 9/2018 | |
| WO | WO-2019022671 A1 * | 1/2019 | ........... A61K 9/1075 |

OTHER PUBLICATIONS

Makrygiannakis et al. Local administration of glucocorticoids decreases synovial citrullination in rheumatoid arthritis. Arthritis Research & Therapy 2012, 14: R20, p. 1-9 (Year: 2012).*
Lewis et al. Current Murine Models of Sepsis. Surgical Infections vol. 17, No. 4, p. 385-393 (Year: 2016).*
U.S. Appl. No. 17/731,833, filed Apr. 28, 2022.
Coumans et al., (2017) "Methodological guidelines to study extracellular Vesicles", Circ. Res., 120(10):1632-1648.
Jeppesen et al., (2014) "Quantitative proteomics of fractionated membrane and lumen exosome proteins from isogenic metastatic and nonmetastatic bladder cancer cells reveal differential expression of EMT factors", Proteomics (14)6:699-712.
Karimi et al., (2018) "Detailed analysis of the plasma extracellular vesicle proteome after separation from lipoproteins", Cell. Mol. Life Sci., 75(15):2873-2886.
Mariantonia et al., (2009) "High levels of exosomes expressing CD63 and caveolin-1 in plasma of melanoma patients. e5219", PLOS ONE, 4(4):1-10.
Matsushita et al., (1989) "Effect of Extracellular pH on the Respiratory Chain and Energetics of Gluconobacter suboxydans", Agricultural and Biological Chemistry,53(11):2895-2902.
Shin et al., (2015) "High-yield isolation of extracellular vesicles using aqueous two-phase system", Scientific Reports, (5)1:1-11.

(Continued)

*Primary Examiner* — Taeyoon Kim

(74) *Attorney, Agent, or Firm* — Shweta Chandra; Bozicevic, Field & Francis LLP

(57) ABSTRACT

The present disclosure provides ghost nanovesicles (gNVs) that are deficient in cytosolic components. Methods of making such vesicles and therapeutic uses of such vesicles are also provided. The gNVs may be used in preventing or treating conditions that may benefit from administration of the gNVs. Such conditions include conditions that involve inflammation.

16 Claims, 11 Drawing Sheets

(56)                    References Cited

OTHER PUBLICATIONS

Tauro et al., (2012) "Two Distinct Populations of Exosomes Are Released from LIM1863 Colon Carcinoma Cell-derived Organoids", Molecular & Cellular Proteomics, 12(3):587-598.

Yoshioka et al., (2014) "Ultra-sensitive liquid biopsy of circulating extracellular vesicles using ExoScreen". Nature Communications, (5)3591:1-8.

D'Atri et al., (2019) "Nano-Ghosts: mesenchymal stem cells derived nanoparticles as a novel approach for cartilage regeneration." Journal of Extracellular Vesicles, vol. 8, 1 page.

Furman et al., (2013) "Reconstructed Stem Cell Nano ghosts: a Natural Tumor Targeting Platform." Nano Letters, vol. 13, No. 7, pp. 3248-3255.

Go et al., (2018) "Extracellular Vesicle-Mimetic Ghost Nanovesicles for Delivering Anti-Inflammatory Drugs to Mitigate Gram-Negative Bacterial Outer Membrane Vesicle-Induced Systemic Inflammatory Response Syndrome." Advance Healthcare Materials, vol. 8, No. 4.

Corrales et al., (2015) "Direct Activation of STING in the Tumor Microenvironment Leads to Potent and Systemic Tumor Regression and Immunity", Cell Reports, 11(7):1018-1030, XP055771217.

Van Der Pol et al. (2015) "Outer membrane vesicles as platform vaccine technology", Biotechnology Journal, 10(11):1689-1706, XP055465407.

Morein et al. (1994) "Separation of inner and outer membrane vesicles from *Escherichia coli* in self-generating Percoll gradients", Analytical Biochemistry, 216(1):47-51, XP055982965.

* cited by examiner

FIG. 1

USE OF GHOST NANOVESICLES AS THERAPEUTICS

CROSS-REFERENCE TO RELATED APPLICATIONS

This application claims the benefit of priority to U.S. Provisional Patent Application No. 62/899,931, filed Sep. 13, 2019, which application is incorporated herein by reference in its entirety.

INTRODUCTION

Vesicles, including microvesicles and nanovesicles, have been described. These vesicles have been used as vaccines or to deliver therapeutics. However, these vesicles have several disadvantages such as lack of a consistent size, non-specific immune response and are produced by methods that lack consistency and reproducibility.

The present disclosure provide nanovesicles that address several aspects of these disadvantages and has many other advantages and therapeutic applications.

SUMMARY

The present disclosure provides ghost nanovesicles (gNVs) that are deficient in cytosolic components. Methods of making such vesicles and therapeutic uses of such vesicles are also provided. The gNVs may be used in preventing or treating conditions that may benefit from administration of the gNVs. Such conditions include conditions that involve inflammation.

BRIEF DESCRIPTION OF DRAWINGS

Figure 1:
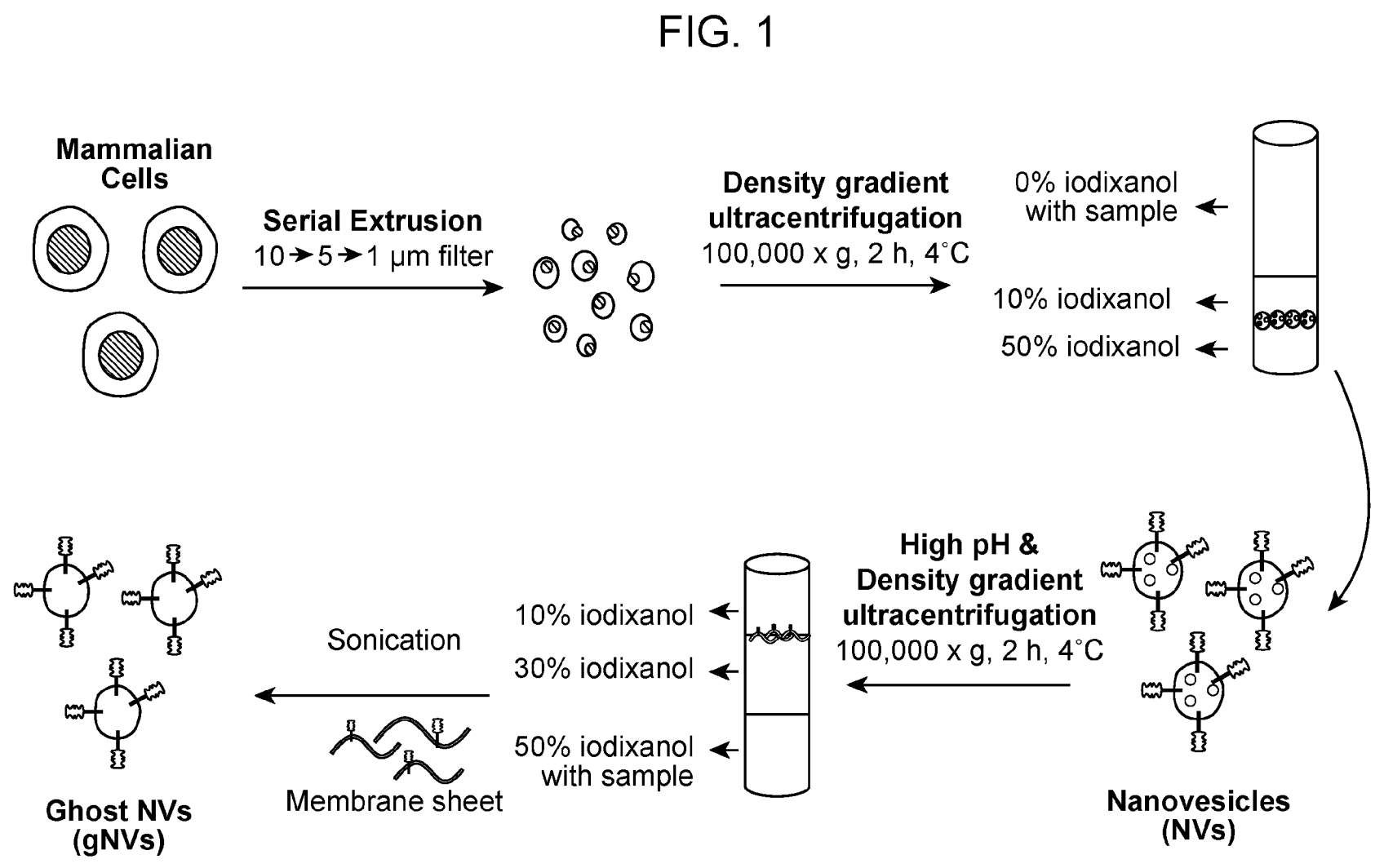

FIG. 1 depicts steps for generation of ghost nanovesicles (gNVs) by extrusion and exposure to alkaline conditions according to an embodiment of the present disclosure.

DEFINITIONS

Figure 2A:
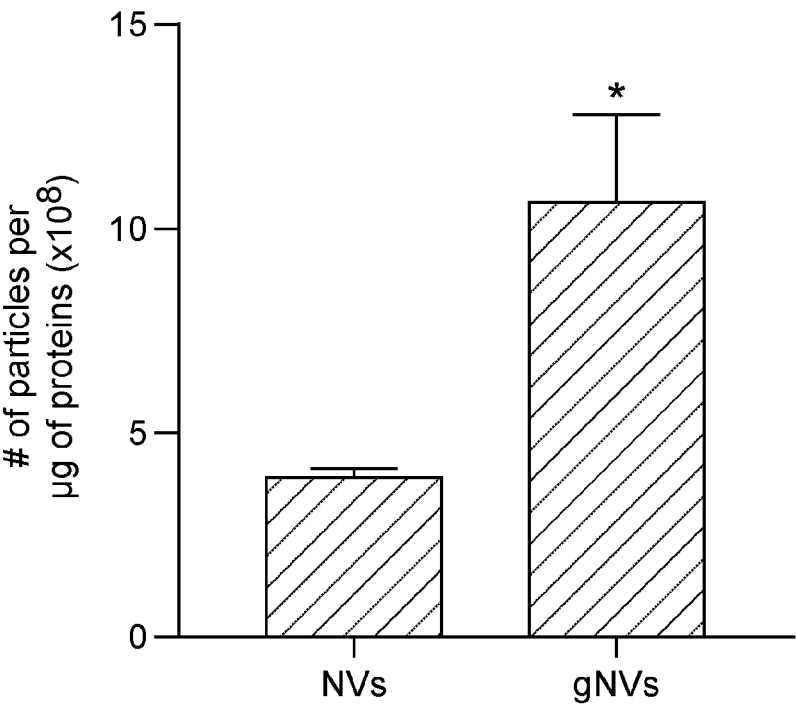
FIGS. 2A and 2B show that gNVs have less contaminants as evident from the increased number of gNV particles per μg of protein (FIG. 2A) and reduced amounts of other debris in preparations compared via imaging (FIG. 2B).
Figure 2B:
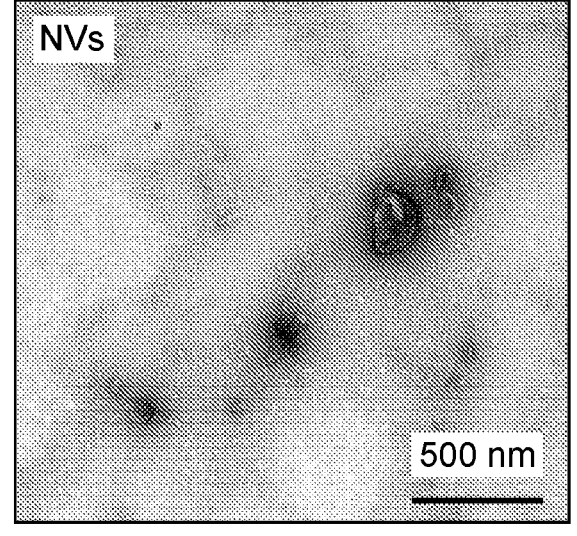
Figure 2B:
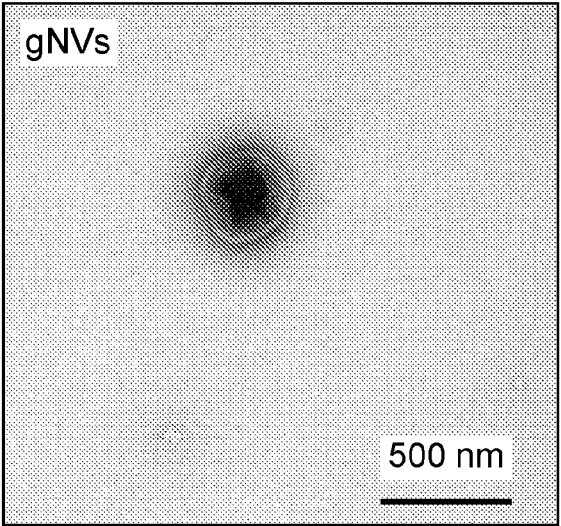
Figure 3A:
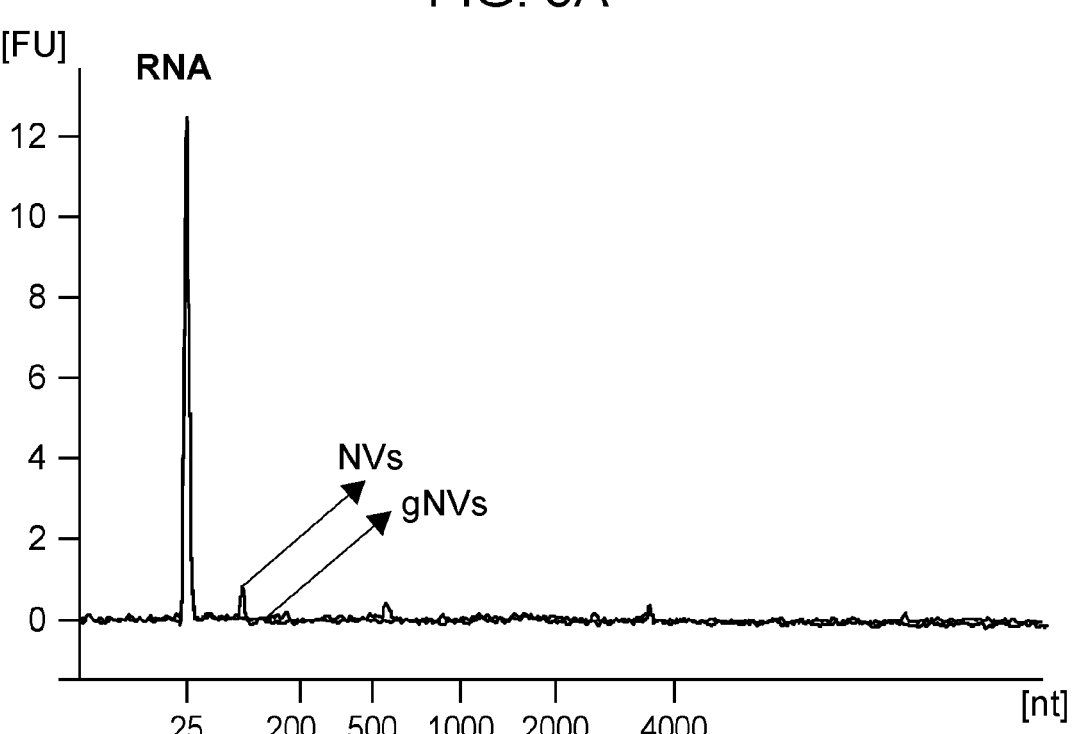
FIGS. 3A and 3B show that the amount of RNA (FIG. 3A) and DNA (FIG. 3B) in gNVs is significantly lower than the amount of RNA and DNA in NVs.
Figure 3B:
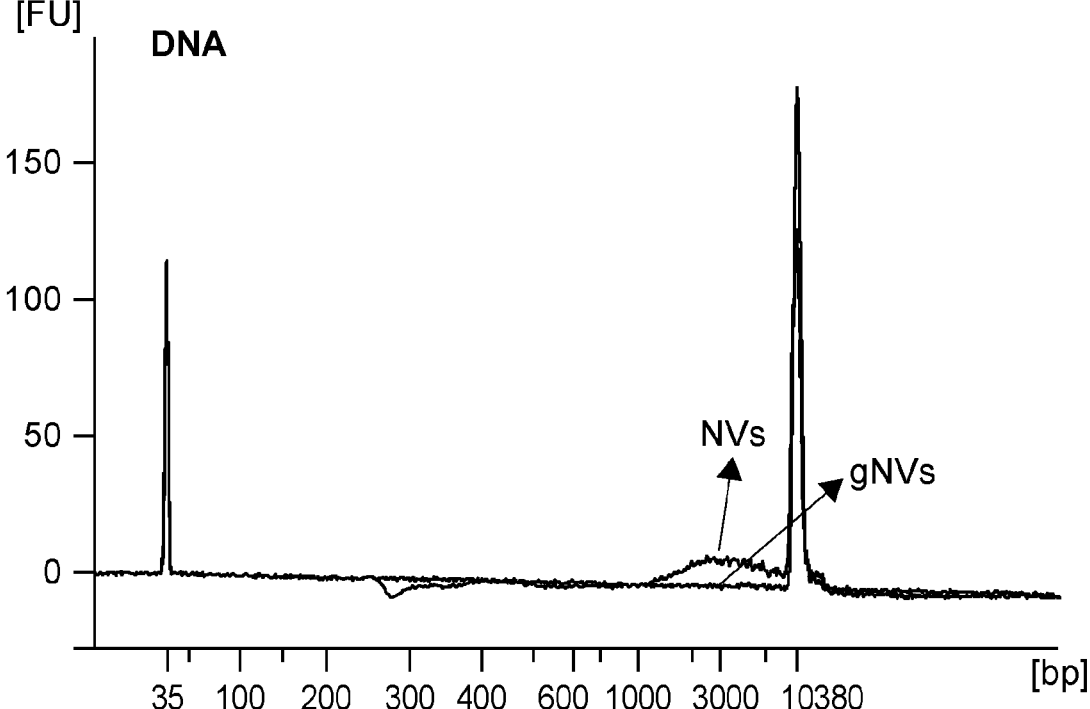

The term "outer membrane vesicle(s)" or "OMV(s)" as used herein refers to vesicles that include an outer membrane enclosing periplasmic contents, cytoplasmic contents and inner membrane components. OMVs include blebs produced by budding of the outer membrane of organisms, such as, gram-negative bacteria. Such OMVs can also be referred to as native OMVs. OMVs can also be produced by disrupting (e.g., by extrusion, sonication, detergents, or osmotic shock) a gram-negative bacterium in a hydrophilic solution thereby forcing the cell to form vesicles.

The term "vesicle" as used herein refers to a spherical structure which contains an interior volume that is separated from the outside environment by a lipid bilayer membrane. A vesicle can be secreted from cells or can be artificially synthesized from a cell. A vesicle is generally smaller than the cell from which it is derived.

The term "revesiculation" and grammatical equivalents thereof, as used herein refers to a process of opening a vesicle, e.g., a cell-derived vesicle, such that the interior contents of the vesicle are released, followed by isolation of the open lipid bilayer membrane, and closing of the open lipid bilayer membrane to reform vesicles. Such vesicles are referred to as ghost vesicles.

The term "non-revesiculated" and grammatical equivalents thereof, as used herein refers to a vesicle, e.g., a cell-derived vesicle that is not a ghost vesicle, i.e., has not been subjected to the process of opening the vesicle such that the interior contents of the vesicle are released, followed by isolation of the open lipid bilayer membrane, and closing of the open lipid bilayer membrane to reform vesicles. Thus, a non-revesiculated vesicle encloses significantly more of the interior contents from the cell from which it is derived as compared to a ghost vesicle prepared from the same type of cell.

The term "deficient" as used in the context of a component present in the ghost nanovesicles (gNVs) derived from a cell as disclosed herein means having at least 50% less of the component, for example, 60%, 70%, 80%, 90%, or 99%, as compared to amount of the component present in non-ghost nanovesicles produced from the same cell. Vesicles that have not been prepared by opening and closing of the vesicles are referred to as nanovesicles.

The term "enriched" as used in the context of a protein (e.g., a membrane protein) present in the gNVs derived from a cell as disclosed herein means that the component makes up a bigger fraction of the total amount of protein in the gNVs as compared to the fraction of the same protein in NVs produced from the same cell type. For example, the enriched protein may represent at least 25% or more of the total proteins in the gNVs while the same protein may represent at most 20% of the total proteins in the NVs. An enriched component may be present in the gNVs at a higher concentration by total weight, e.g., at least a three-fold greater concentration by total weight, e.g., at least 5-fold greater concentration, at least 10-fold greater concentration, at least 30-fold greater concentration, at least 50-fold greater concentration, or at least 100-fold greater concentration than the concentration of that component by total weight in NVs generated from the same cell type from which the gNVs were derived.

As used herein, the term "extracellular vesicle" means a vesicle released by a eukaryotic, e.g., a mammalian cell. Examples of "extracellular vesicles" include exosomes, ectosomes, microvesicles, prostasomes, oncosomes, and apoptotic bodies. As used herein, the term "tumor vesicle" refers to an extracellular vesicle present in a tumor tissue, e.g., released by a tumor cell. A tumor vesicle may be opened and closed to produce a gTV such as ghost tumor micro or nanovesicles (gTMVs or gTNVs). In certain aspects, the gNVs are not generated from extracellular vesicles or tumor vesicles.

Thus, if the concentration of a particular component is 1 microgram per gram of total cell preparation (or of total cell protein), an enriched preparation would contain greater, e.g., at least 3 micrograms of the component per gram of total cell preparation (or of total cell protein).

The term "inflammatory response" as used herein refers to secretion of proinflammatory cytokines, activation of toll-like receptors (TLR) and/or systemic inflammation. Examples of proinflammatory cytokines include –6 IL-2, IL-4, IL-6, IL-12, IL-12p70, IL-17, tumor necrosis factor alpha (TNF-α) and interferon gamma (IFN-γ).

"Isolated" refers to an entity of interest that is in an environment different from that in which it may naturally occur. "Isolated" is meant to include entities that are within samples that are substantially enriched for the entity of interest and/or in which the entity of interest is partially or substantially purified.

The terms "subject" and "patient" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

The terms "treatment," "treat," or "treating," as used herein cover any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

The term "therapeutic effect" refers to some extent of relief of one or more of the symptoms of a disorder (e.g., infection, a neoplasia or tumor) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the vesicles of the present disclosure employed in a pharmaceutical composition at levels lower than that required in order to achieve the desired therapeutic effect and gradually increase the dosage until the desired effect is achieved.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a vesicle" includes a plurality of such vesicles and reference to "the vesicle" includes reference to one or more vesicles and equivalents thereof known to those skilled in the art and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication. Further, the dates of publication provided may be different from the actual publication dates which may need to be independently confirmed.

DETAILED DESCRIPTION

Ghost nanovesicles (gNVs) derived from a mammalian cell, wherein the gNVs are deficient in cytoplasmic proteins and nucleic acids and method of reducing inflammation in a subject in need thereof by administering the gNVs are disclosed.

Ghost nanovesicles and Compositions Thereof

Ghost nanovesicles (gNVs) derived from a mammalian cell, which gNVs are deficient in cytoplasmic proteins and nucleic acids and reduce the levels of at least one proinflammatory cytokine when administered to a subject in need thereof are disclosed.

In certain aspects, the mammalian cell may be an autologous mammalian cell. The autologous cell may be derived from a tissue or organ of the subject. In certain aspects, the mammalian cell may be a heterologous mammalian cell. In certain aspects, the heterologous mammalian cell may be derived from a tissue or organ of a donor, or from a cell line. The tissue or organ from which the mammalian cell is derived may be bone marrow, blood, blood product, adipose tissue, cord blood, fallopian tube, liver, fetal liver or fetal lungs, etc. In certain aspects, the mammalian cell may be monocytes, macrophages, or dendritic cells. In certain aspects, the mammalian cell may not be a cancer cell or a cell derived from a tumor.

In certain aspects, the mammalian cell may be a stem cell. In certain aspects, the mammalian cell may be a cell line, such as, an embryonic stem cell line, an induced pluripotent stem cell or any other cell line. In certain aspects, the stem cell may be an embryonic stem cell or a somatic stem cell such as those found in children and adults. In certain aspects, the mammalian cell may be a hematopoietic stem cell, a mammary stem cell, an intestinal stem cell, an endothelial stem cell, a neural stem cell, an olfactory stem cell, a neural crest stem cell, or a testicular stem cell. In certain aspects, the mammalian cell may be a mesenchymal stem cell. In other aspects, the mammalian cell may be a cell line that has been genetically modified, to change the content and cargo of the gNV.

In certain aspects, the mammalian cell may be genetically modified. The mammalian cell may be genetically modified to express a therapeutic agent, such as, a membrane protein or a lipid that is localized to the plasma membrane. In certain aspects, the mammalian cell may be a cell that naturally produces or is genetically modified to produce one or more therapeutic agents, such as, adhesion molecules, such as, integrins; protein kinases, e.g., tyrosine kinases, serine/threonine kinases; transcription factors; ion channels, e.g., calcium channels, potassium channels, sodium channels; growth factors; interleukins; neurotrophic factors, etc.

In certain aspects, the mammalian cell may be a cell that naturally produces or is genetically modified to produce one or more therapeutic agents, such as, trophic factors, e.g., CDNF, GDNF, neurturin, IGF1, VEGF, HGF; chaperones, e.g., HSP104, HSP70; ephA4; ephA4 ligands; Poly(A) Binding Protein Nuclear 1 (PABPN1); matrin ubiquilin 2; Zinc finger protein 106 (ZFP106); IRE1α kinase/Rnase; ubiquilins; TANK Binding Kinase 1 (TBK1); MuSK agonist antibodies; Ankyrin Repeat And KH Domain Containing 1 (ANKHD1); affitins; Glycerophosphodiester phosphodiesterase 2 (GDE2); MMIF; SRSF1 nuclear transport; anti-mir155; miRNA 125b; miRNA 31; miRNA-206; miRNA 133b; TREM2 activating antibodies; SARM1 inhibitor; macrophage migration inhibitory factor (MIF); dominant negative NFkB; Muscle-Specific Kinase; siRNA targeting tristetraprolin; PPARγ CoActivator 1 alpha; Ret Receptor; notch intracellular domain; TGFβ; INFγ, etc.

The gNVs provided herein retain the membrane proteins which membrane proteins are in substantially native conformation. For example, the gNVs are not exposed to denaturants used as vesiculation agents during generation of the gNVs. For example, the method for making the gNVs does not involve a step of exposing the mammalian cell to a vesiculation agent to form vesicles. In other words, the gNVs are not exposed to vesiculation agents, such as, sulfhydryl blocking agent during or after generation of the gNVs such that the gNVs retain the membrane proteins in their native conformation. The gNVs are not exposed to during or after formation to vesiculation agents such as formaldehyde and dithiothreitol. Sulfhydryl blocking agents include formaldehyde, pyruvic aldehyde, acetaldehyde, glyoxal, glutar aldehyde, acrolein, methacrolein, pyridoxal, N-ethyl malemide (NEM), malemide, chloromercuribenzoate, iodoacetate, potassium arsenite, sodium selenite, thimerosal (merthiolate), benzoyl peroxide, cadmium chloride, hydrogen peroxide, iodosobenzoic acid, meralluride sodium, (mercuhydrin), mercuric chloride, mercurous chloride, chlormerodrin (neohydrin), phenylhydrazine, potassium tellurite, sodium malonate, p-arsenosobenzoic acid, 5,5'-diamino-2,2'-dimethyl arsenobenzene, N,N'-dimethylene sulfonate disodium salt, iodoacetamide, oxophenarsine (mapharsen), auric chloride, p-chloromercuribenzoic acid, p-chloromercuriphenylsulfonic acid, cupric chloride, iodine merbromin (mercuro chrome) porphyrindine, potassium permanganate, mersalyl (salyrgan), silver nitrate, strong silver protein (protargol), uranyl acetate, etc. Other examples of vesiculation agents include cell toxins such as cytochalasin B or melittin.

As used herein, the phrase "not exposed to" in the context of a vesiculation agent means that the gNVs are not exposed to a substantial amount of the vesiculation agent which amount is sufficient to cause generation of vesicles. In other words, the gNVs may be exposed to during or after generation to trace amounts of a vesiculation agent which does not cause denaturation of membrane proteins and does not cause formation of vesicles.

In certain aspects, the gNVs provided herein may be distinguished from gNVs generated by using a vesiculation agent by assaying the vesicles. Assays such as immunoassay or functional assays may be used. In certain aspects, an antibody that binds to a membrane protein in native conformation but does not bind to the protein when it is denatured may be used in an immunoassay to distinguish the gNVs from gNVs made using a vesiculation agent. A functional assay may involve assaying the gNVs for activity of a membrane protein such as binding to a ligand, uptake of a ligand, ability to deliver or pump out a drug or take up a molecule, and the like.

The gNVs may be roughly spherical in shape and may have a diameter smaller than the cells from which the gNVs are produced. In certain aspects, gNVs may be relatively large gNVs that may range in diameter from 100 nm-900 nm, e.g., 100 nm-800 nm, 100 nm-700 nm, 100 nm-600 nm, 100 nm-500 nm, 100 nm-400 nm, 100 nm-300 nm, or 100 nm-200 nm. In certain aspects, gNVs may be relatively small gNVs that may range in diameter from 10 nm-100 nm, e.g., 20 nm-100 nm, 30 nm-100 nm, or 40 nm-100 nm. In certain aspects, a preparation of gNVs, such as a composition of gNVs may include large and small gNVs.

GNVs may be formed by opening nanovesicles (NVs), e.g., by exposing the NVs to high pH, isolating the open sheets of cell membrane, and closing the open sheets of cell membrane to generate the gNVs. In certain aspects, a gNV may be formed by disrupting the mammalian cell to generate vesicles; separating the vesicles using a density gradient and isolating nanovesicles; exposing the isolated nanovesicles to an alkaline pH to open the nanovesicles thereby generating plasma membrane sheets; purifying the plasma membrane sheets; and applying energy to the purified plasma membrane sheets sufficient to convert the plasma membrane sheets into gNVs. NVs formed by such a method includes cytoplasmic components, such as, organelles, cytoplasmic proteins, nucleus, nucleic acids (e.g., RNA, such as, mRNA, miRNA, and the like). A gNV is deficient in such components, i.e., has at least 50% less of the component, for example, 60%, 70%, 80%, 90%, or 99% less, as compared to amount of the component present in a NV that has not been ghost.

In certain aspects, the gNVs are made by adding a therapeutic agent to a composition comprising the purified membrane sheets and applying energy to the composition sufficient to convert the plasma membrane sheets into gNVs comprising the therapeutic agent. In certain aspects, the therapeutic agent does not comprise an anti-inflammatory agent.

In certain aspects, the gNVs may be loaded with a therapeutic agent that is a nucleic acid, peptide, or protein. The therapeutic agent may be an antibody, a growth factor (e.g., EGF, FGF, VEGF, etc.), siRNA, miRNA, shRNA, etc. In certain aspects, the therapeutic agent may be an anticancer agent or an angiogenesis inhibitor. In certain aspects, the anticancer agent may be DNA alkylating agents, such as mechlorethamine, chlorambucil, phenylalanine, mustard, cyclophosphamide, ifosfamide, carmustine (BCNU), lomustine (CCNU), streptozotocin, busulfan, thiotepa, cisplatin and carboplatin, anti-cancer antibiotics, such as dactinomycin (actinomycin D), doxorubicin (adriamycin), epirubicin, idarubicin, mitoxantrone, plicamycin, mitomycin and C Bleomycin, and plant alkaloids, such as vincristine, vinblastine, paclitaxel, docetaxel, daunorubicin, taxol, oncovin, prednisone, cisplatin, herceptin, rituximab, etoposide, teniposide, topotecan and iridotecan.

In certain aspects, gNV may be enriched in membrane proteins, such as, proteins localized in the plasma membrane, e.g., transport proteins. "Enriched" in the context of a component enriched in the gNVs disclosed herein means that the enriched component is present in the gNVs at a higher concentration by total weight, e.g., at least a three-fold greater concentration by total weight, e.g., at least 5-fold greater concentration, at least 10-fold greater concentration, at least 30-fold greater concentration, at least 50-fold greater concentration, or at least 100-fold greater concentration than the concentration of that component by total weight in NVs from which the gNVs are derived.

In certain aspects, compositions that include the gNVs are provided. The compositions may include the gNVs and a carrier, diluent, vehicle, excipient, and the like. In certain aspects, the compositions of the present disclosure may include the gNVs and a pharmaceutically acceptable carrier, diluent, vehicle, excipient, and the like. In certain aspects, the compositions may further include an additional prophylactic or therapeutic agent. In certain aspects, the compositions may gNVs in an amount effective for reducing inflammation in a subject in need thereof. In certain aspects, the compositions may gNVs derived from different cells and/or loaded with different therapeutic agents. For example, the gNVs may be derived from two, three, four, or more different types of cells. In certain aspects, the composition may include a first type of gNV that includes a first therapeutic agent and a second type of gNV that includes a second therapeutic agent, and so on.

A carrier, diluent, vehicle, excipient, and the like may be salt, buffer, antioxidant (e.g., ascorbic acid and sodium bisulfate), preservative (e.g., benzyl alcohol, methyl parabens, ethyl or n-propyl, p-hydroxybenzoate), emulsifying agent, suspending agent, dispersing agent, solvent, filler, bulking agent, detergent, and/or adjuvant. For example, a suitable vehicle may be physiological saline solution or buffered saline, possibly supplemented with other materials common in pharmaceutical compositions for, e.g., parenteral administration. Neutral buffered saline or saline mixed with serum albumin are further exemplary vehicles. Those skilled in the art will readily recognize a variety of buffers that could be used in the compositions. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-amino-propanesulfonic acid (TAPS). In certain aspects, an adjuvant included in the disclosed compositions may be poly-ICLC, 1018 ISS, aluminum salts, Amplivax, AS15, BCG, CP-870, 893, CpG7909, CyaA, dSLIM, GM-CSF, 1030, 1031, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, SRL172, Virosomes and other Virus-like particles, YF-17D, VEGF trap, R848, beta-glucan, Pam3Cys, acrylic or methacrylic polymers, or copolymers of maleic anhydride and Aquila's QS21 stimulon.

In certain aspects, the gNVs, may be loaded with therapeutic agents, e.g., chemotherapeutic agents, anti-cancer antibodies, and the like. In certain aspects, the gNVs disclosed herein may not be loaded with therapeutic agents. In certain aspects, the gNVs disclosed herein may not be loaded an anti-inflammatory agent. In certain aspects, the gNVs disclosed herein may not be administered with an anti-inflammatory agent.

In certain aspects, the compositions comprising the gNVs as disclosed herein may not include an effective amount of an adjuvant, such as, those used to enhance immunogenicity of a composition.

In certain aspects, the gNV and compositions thereof find use in a method for reducing at least one proinflammatory cytokine in a subject in need thereof, the method comprising administering the composition to the subject. Such methods are described in detail in the following section.

Methods

In certain aspects, a method for treating a subject in need thereof is provided. In certain aspects, a method for reducing inflammation in a subject in need thereof is provided. The method may include administering to the subject an effective amount of ghost nanovesicles (gNVs) derived from a mammalian cell, wherein the gNVs are deficient in cytoplasmic proteins and nucleic acids, wherein the gNVs reduce the levels of at least one proinflammatory cytokine in the subject.

The term "reduced" in the context of inflammatory response means production of a lower level of a proinflammatory cytokine in the presence of the gNVs as compared to that produced in absence of the gNVs. In some embodiments, production of cytokines is lowered by at least 5%, for example, at least 10%, at least 20%, at least 30%, at least 40%, at least 50%, at least 60% or more as compared to that produced in absence of administration of gNVs. The at least one proinflammatory cytokine may include one or more of IL-2, IL-4, IL-6, IL-12, IL-12p70, IL-17, tumor necrosis factor alpha (TNF-α), or interferon gamma (IFN-γ). The mammalian cell from which the gNVs are derived may be as described in the preceding section providing description of the gNVs of the present disclosure.

In certain aspects, the gNVs may be made by a method that includes disrupting the mammalian cell to generate vesicles; separating the vesicles based on density and isolating nanovesicles; exposing the isolated nanovesicles to an alkaline pH to open the nanovesicles thereby generating plasma membrane sheets; purifying the plasma membrane sheets; and applying energy to the purified plasma membrane sheets sufficient to convert the plasma membrane sheets into gNVs.

In certain aspects, the method may include adding a therapeutic agent to a composition comprising the purified membrane sheets and applying energy to the composition sufficient to convert the plasma membrane sheets into gNVs comprising the therapeutic agent. In certain aspects, the therapeutic agent does not comprise an anti-inflammatory agent. In certain aspects, the gNVs do not include a substantial amount of an anti-inflammatory agent, for example, the gNVs may include a trace amount of an anti-inflammatory agent. In certain aspects, a composition comprising the gNVs is substantially free of an anti-inflammatory agent.

In certain aspects, disrupting the mammalian cell to generate vesicles may involve mechanical, electrical or chemical methods for cytolysis. Examples of techniques for cytolysis include osmosis, electroporation, sonication, homogenization, detergent treatment, freeze-thawing, extrusion, mechanical degradation, and chemical treatment, but are not limited thereto. In certain aspects, the mammalian cell is not disrupted by detergent treatment. In a mechanical degradation method, a solution of mammalian cells is shaken together with metal, ceramic or sufficiently hard plastic balls. In certain aspects, disrupting the mammalian cell may include applying a shear force to the mammalian cell. Shear force may be applied by extruding the mammalian cell. Extrusion may include forcing the mammalian cells through pores smaller than the size of the mammalian cells. In the context of extrusion, mammalian cells may be forced to sequentially pass through a series of filters having decreasing pore sizes. For example, mammalian cells are sequentially passed through three filters with respective pore sizes of 10 μm→5 μm→1 μm to form vesicles.

In certain aspects, disrupting the mammalian cell may include applying acoustic energy to the mammalian cell. Acoustic energy may be applied via a sonication device. Sonication conditions may be adjusted for the desired disruptive energy. For example, low temperature, low energy, and/or short duration for sonication may be used when disrupting spheroplasts to generate vesicles. Sonication can be performed with different degree of intensity, including low energy sonication over periods of 1 minute to 3 hours. In certain aspects, sonication may be performed using an ultrasonic probe-type device. In certain aspects, an ultrasonic bath may be used for sonication. The duration of sonication may be adjusted based on the type of device being used to perform the sonication. For example, an ultrasonic probe-type device may provide about 1000 times higher energy than an ultrasonic bath. In certain aspects, ultrasonic probe-type device may be used for disrupting the mammalian cell.

Following disruption of the mammalian cells to generate vesicles, such as, vesicles that have the plasma membrane enclosing cytosolic contents, these vesicles may be isolated from any remaining mammalian cells. Separation of these vesicles from mammalian cells may be performed using differences in size, density, buoyancy, etc. In certain aspects, centrifugation (e.g., density gradient centrifugation or density gradient ultracentrifugation) or filtration may be performed to isolate the vesicles. In certain aspects, the vesicles may be purified using density gradient ultracentrifugation, where vesicles present in between 10% and 50% density gradient may be isolated. The vesicles present in between 10% and 50% density gradient are mostly nanometer sized vesicles or nanovesicles.

The isolated nanovesicles may then be exposed to an alkaline solution to open up the nanovesicles which expels the cytoplasmic content of the nanovesicles. In certain aspects, the alkaline solution used for opening the nanovesicles may have a pH of 11-14. An alkaline solution for opening the nanovesicles may be prepared a sodium carbonate ($Na_2CO_3$), sodium hydroxide (NaOH), ammonia ($NH_3$), calcium hydroxide ($Ca(OH)_2$), potassium hydroxide (KOH), sodium hydrogen carbonate ($NaHCO_3$), or magnesium hydroxide ($Mg(OH)_2$) solution. The duration of incubation of the nanovesicles in an alkaline solution may be adjusted based on the number of nanovesicles, total volume of the solution, and the like. As used herein the step of incubating or exposing vesicles to an alkaline pH may include using an alkaline solution having a pH of 9-14, e.g., pH of 10-14, pH of 11-14, pH of 12-14, or pH of 13-14.

Plasma membrane sheets generated from opening of nanovesicles may be separated from whole nanovesicles (i.e., unopened) by utilizing any suitable separation method. In certain aspects, purifying the plasma membrane sheets may involve centrifugation, e.g., centrifugation (such as, density gradient centrifugation or density gradient ultracentrifugation), filtration, or another suitable method, such as size exclusion, dialysis, tangential flow filtration and the like. In certain aspects, the plasma membrane sheets may be purified using density gradient ultracentrifugation, where plasma membrane sheets present in between 10% and 30% density gradient may be isolated. The plasma membrane sheets present in between 10% and 30% density gradient are substantially free of nanovesicles.

In certain aspects, the method of generating the gNVs may be involve applying energy or force to the purified plasma membrane sheets sufficient to convert the plasma membrane sheets into gNVs. Suitable sources of energy include mild sonication, shear force, acoustic force, freeze-thaw, and the like. In certain aspects, the purified plasma membrane sheets may be sonicated for a duration of time sufficient to convert the plasma membrane sheets into gNVs. In certain aspects, the purified plasma membrane sheets may be sonicated by applying energy 100-1000 times less than that applied for disrupting mammalian cells. In certain aspects, mild sonication may include using an ultrasonic bath for converting the plasma membrane sheets into gNVs.

In certain aspects, the gNVs of the present disclosure may be prepared by the method depicted in FIG. 1. As shown in FIG. 1, a mammalian cell may be disrupted by serial extrusion through filters of increasingly small pores, forcing the cells to break into vesicles. Separating the vesicles based on size using density gradient ultracentrifugation using a density gradient of from 0% to 50% iodixanol. Isolating nanovesicles present between 10% and 50% density layers; exposing the nanovesicles to an alkaline solution (e.g., pH11-pH14) to open the NVs; separating the opened NVs using density gradient ultracentrifugation by using a density gradient of from 10% to 50% iodixanol. Isolating opened NVs (i.e., membrane sheets) present between 10%-30% density layers; and sonicating the isolated membrane sheets to generate gNVs.

The subject in need of reduction of inflammation may have or may be susceptible to developing an inflammatory related condition. The inflammatory related condition may be cancer, multiple sclerosis, psoriasis, dry eye disease, asthma, sepsis, infection, Rheumatoid arthritis, ulcerative colitis, Crohn's disease, tuberculosis, hepatitis, sinusitis, autoimmune disease, inflammatory bowel disease, pelvic inflammatory disease, ulcers, atherosclerosis, erythema, necrosis, vasculitis, ankylosing spondylitis, connective tissue disease, kidney disease, sarcoidosis, thyroiditis, osteoarthritis, Rheumatism, chronic inflammatory condition, demyelinating polyneuropathy, pancreatitis, psoriatic arthritis, periodontitis, Behcet's disease, sinusitis, polymyalgia rheumatic, nephritis, diverticulitis, granulomatosis with polyangilitis, granuloma, encephalitis, immune-mediated inflammatory disease, esophagitis, gout, uveitis, myopathy, gallbladder disease, periodic fever syndrome, interstitial cystitis, peritonitis, appendicitis, neurodegenerative disease, Parkinson's disease, Alzheimer's, cerebellar ataxias, systemic lupus erythematous, fibromyalgia, diverticulitis, dermatitis, spinobulbar muscular atrophy (SBMA), lysosomal storage diseases, cerebral palsy, glioma, glioblastoma, muscular dystrophy, ataxia telangiectasia (AT), schizophrenia, depression, bipolar disorder, attention deficit disorder, trisomy 21, amyotrophic lateral sclerosis (ALS) and ankylosing spondylitis. In certain aspects, the inflammatory related condition may be asthma. In certain aspects, the inflammatory related condition may be sepsis. In certain aspects, the inflammatory related condition may be infection. In certain aspects, the inflammatory related condition may be bacterial, viral or parasitic infection.

In certain aspects, the method of reducing inflammation may include administering an additional therapeutic agent to the subject. In certain aspects, the additional therapeutic agent is present in the gNVs. In certain aspects, the method comprises administering a composition comprising the additional therapeutic agent and the gNVs. In certain aspects, the method comprises administering the additional therapeutic agent in conjunction with the gNVs, such as, co-administering (as a single composition or administering at substantially the same time) or administering the gNVs and the additional therapeutic agent sequentially.

The therapeutic agent may be a small molecule, a peptide, a nucleic acid, or a polypeptide. The therapeutic agent may be as provided in the preceding section. The therapeutic agent may have a general anti-inflammatory property, or may target different steps of inflammatory pathways in the cell, such as downstream TLR-receptor activation (Myd88 or NFKB), downstream of cytokine receptors, or Stimulator of Interferon Gens (STING) pathways.

Administration of gNVs

The present disclosure contemplates the administration of the disclosed compositions in any appropriate manner for prevention and/or treatment of a condition as described herein. Suitable routes of administration include parenteral (e.g., intramuscular, intravenous, intraarterial, subcutaneous (e.g., injection), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation, as well as injection directly into a diseased tissue, for example a tumor tissue.

In certain aspects, the administering comprises local administration to a target site in the subject. In certain aspects, the target site comprises or is susceptible to developing an inflammatory response. In certain aspects, the target site has an injury. The target site may be adjacent to a site that has injury. The target site may include a site in the central nervous system. The target site may be brain. The target site may have an arterial blockage. In certain aspects, the administering may be intraarterial administering at the site of arterial blockage, e.g., a catheter used for clot retrieval may be used to administer the gNVs after clot retrieval.

In certain aspects, the compositions of gNVs may be injected into or adjacent a tumor. In certain aspects, a composition of an anticancer agent and a composition of gNVs may be administered simultaneously to a subject.

The present disclosure contemplates methods wherein the compositions of the present disclosure is administered to a subject at least twice daily, at least once daily, at least once every 48 hours, at least once every 72 hours, at least once weekly, at least once every 2 weeks, or once monthly.

Combination Therapy

The present disclosure contemplates the use of the compositions provided herein in combination with one or more active therapeutic agents or other prophylactic or therapeutic modalities. In such combination therapy, the various active agents frequently have different mechanisms of action. Such combination therapy may be especially advantageous by allowing a dose reduction of one or more of the agents, thereby reducing or eliminating the adverse effects associated with one or more of the agents; furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, compositions of the present disclosure are administered or applied sequentially, e.g., where one agent is administered prior to one or more other agents. In other embodiments, the compositions are administered simultaneously, e.g., where two or more compositions are administered at or about the same time; the two or more compositions may be present in two or more separate formulations or combined into a single formulation (i.e., a co-formulation). Regardless of whether the two or more compositions are administered sequentially or simultaneously, they are considered to be administered in combination for purposes of the present disclosure.

The compositions of the present disclosure can be used in combination with other agents useful in the treatment, prevention, suppression or amelioration of the diseases, disorders or conditions set forth herein, including those that are normally administered to subjects suffering from inflammation.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method for reducing inflammation in a subject in need thereof, the method comprising:

administering to the subject an effective amount of ghost nanovesicles (gNVs) derived from a mammalian cell, wherein the gNVs are deficient in cytoplasmic proteins and nucleic acids, wherein the gNVs reduce the levels of at least one proinflammatory cytokine in the subject.

2. The method of aspect 1, wherein the mammalian cell is an autologous mammalian cell.

3. The method of aspect 1, wherein the mammalian cell is a heterologous mammalian cell.

4. The method of any one of aspects 1-3, wherein the mammalian cell is a stem cell.

5. The method of any one of aspects 1-4, wherein the mammalian cell is genetically modified.

6. The method of any one of aspects 1-5, wherein the mammalian cell comprises a therapeutic agent, wherein optionally the therapeutic agent does not comprise an anti-inflammatory agent.

7. The method of any one of aspects 1-6, wherein the gNVs are large gNVs having a diameter of 100 nm-200 nm.

8. The method of any one of aspects 1-6, wherein the gNVs are small gNVs having a diameter of 40 nm-100 nm.

9. The method of any one of aspects 1-6, wherein the gNVs are comprise large gNVs having a diameter of 100 nm-200 nm and small gNVs having a diameter of 40 nm-100 nm.

10. The method of any one of aspects 1-9, wherein the gNVs are made by a method comprising:

disrupting the mammalian cell to generate vesicles;

separating the vesicles based on density and isolating nanovesicles;

exposing the isolated nanovesicles to an alkaline pH to open the nanovesicles thereby generating plasma membrane sheets;

purifying the plasma membrane sheets; and applying energy to the purified plasma membrane sheets sufficient to convert the plasma membrane sheets into gNVs.

11. The method of aspect 10, further comprising adding a therapeutic agent to a composition comprising the purified membrane sheets and applying energy to the composition sufficient to convert the plasma membrane sheets into gNVs comprising the therapeutic agent wherein optionally, the therapeutic agent does not comprise an anti-inflammatory agent.

12. The method of any one of aspects 1-11, wherein the at least one proinflammatory cytokine comprises IL-2, IL-4, IL-6, IL-12, IL-12p70, IL-17, tumor necrosis factor alpha (TNF-α), or interferon gamma (IFN-γ).

13. The method of any one of aspects 1-12, wherein the subject has or is susceptible to developing an inflammatory related condition selected from the group consisting of cancer, multiple sclerosis, psoriasis, dry eye disease, asthma, sepsis, infection, Rheumatoid arthritis, ulcerative colitis, Crohn's disease, tuberculosis, hepatitis, sinusitis, autoimmune disease, inflammatory bowel disease, pelvic inflammatory disease, ulcers, atherosclerosis, erythema, necrosis, vasculitis, ankylosing spondylitis, connective tissue disease, kidney disease, sarcoidosis, thyroiditis, osteoarthritis, Rheumatism, chronic inflammatory condition, demyelinating polyneuropathy, pancreatitis, psoriatic arthritis, periodontitis, Behcet's disease, sinusitis, polymyalgia rheumatic, nephritis, diverticulitis, granulomatosis with polyangilitis, granuloma, encephalitis, immune-mediated inflammatory disease, esophagitis, gout, uveitis, myopathy, gallbladder disease, periodic fever syndrome, interstitial cystitis, peritonitis, appendicitis, Parkinson's disease, Alzheimer's, systemic lupus erythematous, fibromyalgia, diverticulitis, dermatitis and ankylosing spondylitis.

14. The method of aspect 13, wherein the inflammatory related condition is asthma.

15. The method of aspect 13, wherein the inflammatory related condition is sepsis.

16. The method of aspect 13, wherein the inflammatory related condition is infection.

17. The method of aspect 13, wherein the infection is a bacterial, viral or parasitic infection.

18. The method of any one of aspects 1-17, wherein the method further comprises administering a therapeutic agent to the subject.

19. The method of aspect 18, wherein the method comprises administering a composition comprising the gNVs and the therapeutic agent to the subject.

20. The method of aspect 18 or 19, wherein the therapeutic agent comprises a small molecule, a peptide, a nucleic acid, or a polypeptide.

21. The method of aspect 18 or 19, wherein the therapeutic agent comprises an antibody.

22. The method of any one of aspects 1-21, wherein the administering comprises intravenous administration.

23. The method of any one of aspects 1-21, wherein the administering comprises subcutaneous administration.

24. The method of any one of aspects 1-21, wherein the administering comprises intramuscular, intraperitoneal, intraarterial, intraarticular, intracerebral (intraparenchymal) or intracerebroventricular administration.

25. The method of any one of aspects 1-21, wherein the administering comprises local administration to a target site in the subject.

26. The method of aspect 25, wherein the target site comprises or is susceptible to developing an inflammatory response.

27. The method of aspect 25 or 26, wherein the target site has an injury.

28. The method of aspect 25 or 26, wherein the target site is adjacent to a site that has injury.

29. The method of aspect 27-28, wherein the target site comprises a site in the central nervous system.

30. The method of aspect 29, wherein the target site comprises brain.

31. The method of aspect 30, wherein the target site comprises site of arterial blockage.

32. The method of aspect 31, wherein the administering is intraarterial administering.

33. The method of any one of aspects 1-31, wherein the gNVs are not derived from a cancer cell.

34. The method of any one of aspects 1-31, wherein the gNVs are not derived from a tumor.

35. The method of any one of aspects 1-31, wherein the gNVs are derived from an isolated mammalian cell present in a composition deficient in vesicles released from cells.

36. A composition comprising:

ghost nanovesicles (gNVs) derived from a mammalian cell, wherein the gNVs are deficient in cytoplasmic proteins and nucleic acids, wherein the gNVs reduce the levels of at least one proinflammatory cytokine when administered to a subject in need thereof.

37. The composition of aspect 36, wherein the mammalian cell is an autologous mammalian cell.

38. The composition of aspect 36, wherein the mammalian cell is a heterologous mammalian cell.

39. The composition of any one of aspects 36-38, wherein the mammalian cell is a stem cell.

40. The composition of any one of aspects 36-39, wherein the mammalian cell is genetically modified.

41. The composition of any one of aspects 36-40, wherein the mammalian cell comprises a therapeutic agent, wherein optionally the therapeutic agent does not comprise an anti-inflammatory agent.

42. The composition of any one of aspects 36-41, wherein the gNVs are large gNVs having a diameter of 100 nm-200 nm.

43. The composition of any one of aspects 36-41, wherein the gNVs are small gNVs having a diameter of 40 nm-100 nm.

44. The composition of any one of aspects 36-41, wherein the gNVs are comprise large gNVs having a diameter of 100 nm-200 nm and small gNVs having a diameter of 40 nm-100 nm.

45. The composition of any one of aspects 36-44, wherein the gNVs are made by a method comprising:

disrupting the mammalian cell to generate vesicles;

separating the vesicles based on density and isolating nanovesicles;

exposing the isolated nanovesicles to an alkaline pH to open the nanovesicles thereby generating plasma membrane sheets;

purifying the plasma membrane sheets; and applying energy to the purified plasma membrane sheets sufficient to convert the plasma membrane sheets into gNVs.

46. The composition of aspect 45, wherein the gNVs are made by adding a therapeutic agent to a composition comprising the purified membrane sheets and applying energy to the composition sufficient to convert the plasma membrane sheets into gNVs comprising the therapeutic agent, wherein optionally, the therapeutic agent does not comprise an anti-inflammatory agent.

47. The composition of any one of aspects 36-46, wherein the at least one proinflammatory cytokine comprises IL-2, IL-4, IL-6, IL-12, IL-12p70, IL-17, tumor necrosis factor alpha (TNF-α), or interferon gamma (IFN-γ).

48. The composition of any one of aspects 36-46 for use in a method for reducing at least one proinflammatory cytokine in a subject in need thereof, the method comprising administering the composition to the subject.

49. The composition of aspect 48, wherein the subject has or is susceptible to developing an inflammatory related condition selected from the group consisting of cancer, multiple sclerosis, psoriasis, dry eye disease, asthma, sepsis, infection, Rheumatoid arthritis, ulcerative colitis, Crohn's disease, tuberculosis, hepatitis, sinusitis, autoimmune disease, inflammatory bowel disease, pelvic inflammatory disease, ulcers, atherosclerosis, erythema, necrosis, vasculitis, ankylosing spondylitis, connective tissue disease, kidney disease, sarcoidosis, thyroiditis, osteoarthritis, Rheumatism, chronic inflammatory condition, demyelinating polyneuropathy, pancreatitis, psoriatic arthritis, periodontitis, Behcet's disease, sinusitis, polymyalgia rheumatic, nephritis, diverticulitis, granulomatosis with polyangilitis, granuloma, encephalitis, immune-mediated inflammatory disease, esophagitis, gout, uveitis, myopathy, gallbladder disease, periodic fever syndrome, interstitial cystitis, peritonitis, appendicitis, Parkinson's disease, Alzheimer's, systemic lupus erythematous, fibromyalgia, diverticulitis, dermatitis and ankylosing spondylitis.

50. The composition of aspect 49, wherein the inflammatory related condition is asthma, sepsis, or infection, wherein optionally the infection is bacterial, viral or parasitic infection.

51. The composition of aspect 41, wherein the therapeutic agent comprises a small molecule, a peptide, a nucleic acid, or a polypeptide.

52. The composition of aspect 41, wherein the therapeutic agent comprises an antibody.

53. The composition of any one of aspects 36-52, wherein the gNVs are not derived from a cancer cell.

54. The composition of any one of aspects 36-52, wherein the gNVs are not derived from a tumor.

55. The composition of any one of aspects 36-52, wherein the gNVs are derived from an isolated mammalian cell present in a composition deficient in vesicles released from cells.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Generation of gNVs from Mesenchymal Stem Cells

Methods

Preparation of gNVs

MSCs were resuspended at a density of $5 \times 10^6$ cells per mL in total 10 mL of phosphate buffered saline. Cell suspensions were passed five times through each of the membrane filters with a pore size of 10 μm, 5 μm and 1 μm, in that order. Respectively 1 and 2 mL of 50 and 10% solution of iodixanol (Axis-Shield PoC AS), followed by 7 mL of the cell suspension effluent from the membrane filter were sequentially added to each 10 mL ultracentrifuge tube. The layers formed between 50% iodixanol and 10% iodixanol after ultracentrifugation at 100,000×g for 2 hours were collected and considered NVs. The NVs were incubated with high pH solution (200 mM $Na_2CO_3$, pH 14.0) for 1 hour at 25 degree. The solution was applied to 4 mL of 50% iodixanol, followed by addition of 4 mL of 30% iodixanol and 2 mL of 10% iodixanol to ultracentrifuge tube. The layers formed between 10% and 30% iodixanol after ultracentrifugation at 100,000×g for 2 hours was collected. Finally, the samples were sonicated for 30 min, and considered gNVs (FIG. 1).

Preparation of OMVs

*E. coli* cultures were pelleted at 6,000×g, 4° C. for 20 min, twice, and then the supernatant fraction was filtered through a 0.45-µm vacuum filter and was concentrated by ultrafiltration Vivaflow 200 module (Sartorius) with a 100 kDa cut-off membrane. The retentate was again filtered through a 0.22-µm vacuum filter to remove any remaining cells. The resulting filtrate was subjected to ultracentrifugation at 150,000×g, 4° C. for 3 h and resuspended in PBS.

RNA and DNA Analysis

RNA from NVs and gNVs was isolated using miR-CURY™ RNA isolation kit for biofluids (Exiqon) according to manufacturer's protocol. DNA was isolated using Qiamp DNA Blood Mini kit (Qiagen) according to manufacturer's protocol. One microliter of isolated RNA or DNA were analyzed for its quality, yield, and nucleotide length with capillary electrophoresis using Agilent RNA 6000 Nanochip and Agilent High sensitivity DNA chip, respectively, on an Agilent 2100 Bioanalyzer® (Agilent Technologies).

Example 2: Proteomic Analysis of gNVs

LC-MS/MS Analysis

NVs and gNVswere digested with trypsin using the filter-aided sample preparation (FASP) method and C18 spin columns desalting according to manufacturer's instructions. All fractions were dried on Speedvac and reconstituted in 3% acetonitrile and 0.2% formic acid and analyzed on Orbitrap Fusion Tribrid mass spectrometer interfaced with Easy-nLC 1200 (Thermo Fisher Scientific, Waltham, MA). Peptides were trapped on the Acclaim Pepmap 100 C18 trap column (100 µm×2 cm, particle size 5 µm; Thermo Fischer Scientific) and separated on the in-house packed C18 analytical column (75 µm×30 cm, particle size 3 µm) using the gradient from 5% to 33% B in 160 min, from 33% to 100% B in 5 min, solvent A was 0.2% formic acid and solvent B was 80% acetonitrile and 0.2% formic acid. Precursor ion mass spectra were recorded at 120 000 resolution, the most intense precursor ions were selected, fragmented using HCD at collision energy setting of 30 and the MS/MS spectra were recorded at 30 000 resolution with the maximum injection time of 125 ms and the isolation window of 1.0 Da. Charge states 2 to 7 were selected for fragmentation, dynamic exclusion was set to 45 s with 10 ppm tolerance.

Results

Figures 4A, 4B:
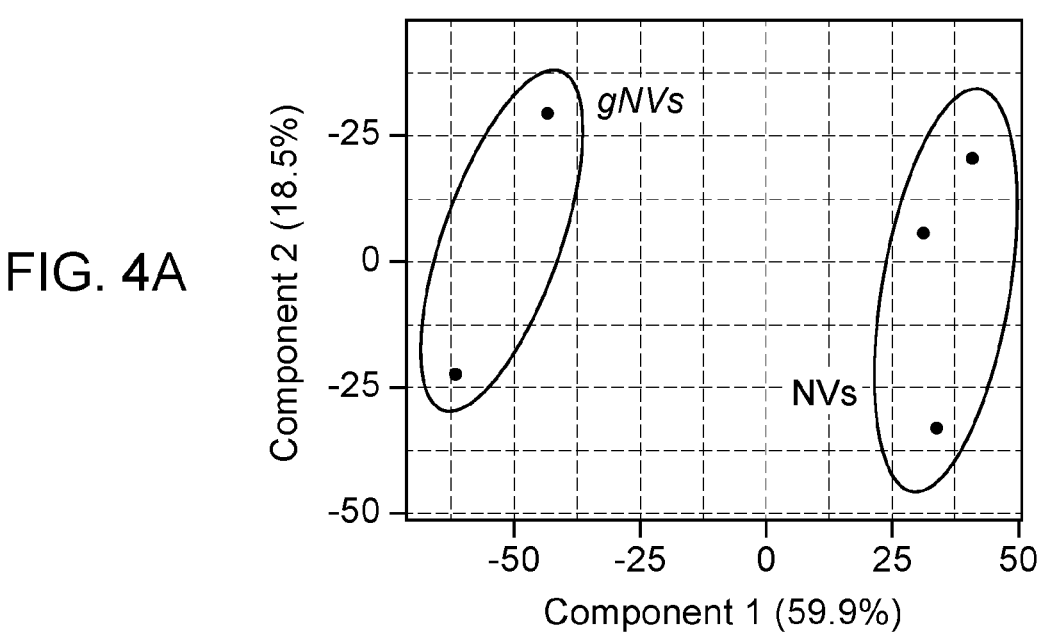
FIGS. 4A and 4B depict comparative proteomics between NVs and gNVs, showing that NVs and gNVs have unique quantification profile.
Figure 5A:
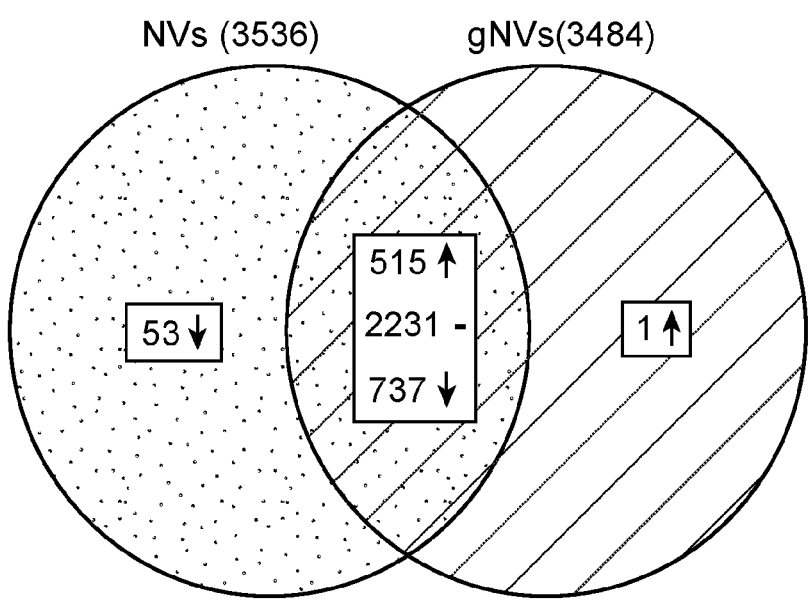
FIG. 5A and FIG. 5B depict protein profile of NVs and gNVs. There are three groups based on 1.5 fold or higher change: 1) NV-enriched protein, 2) gNV-enriched protein; and 3) common protein.
Figure 5B:
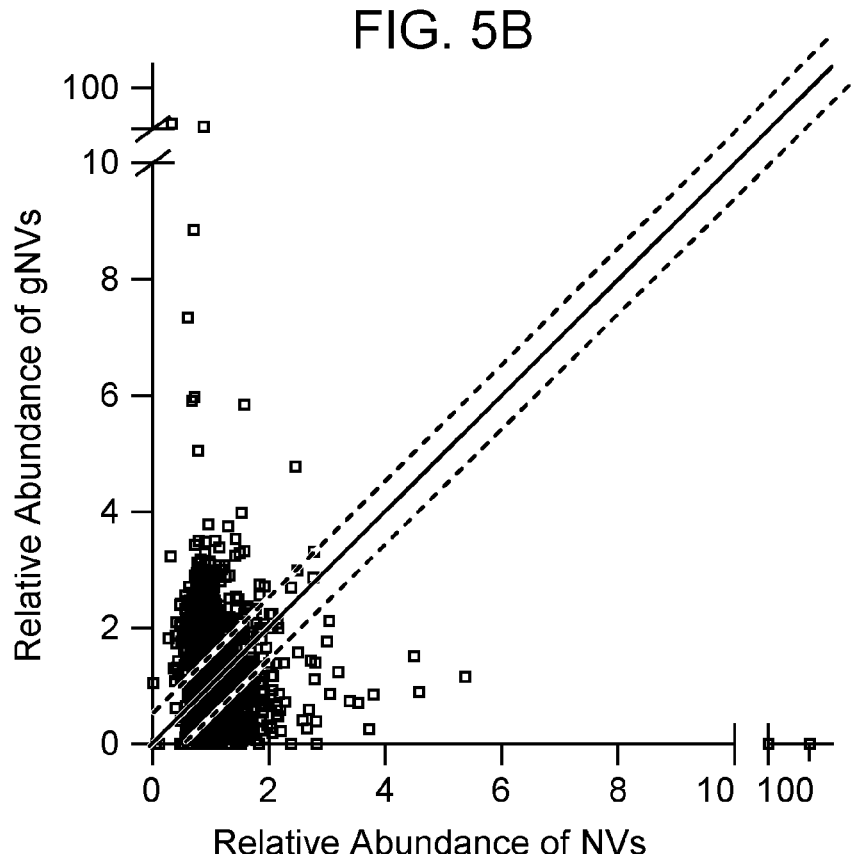
Figure 6:
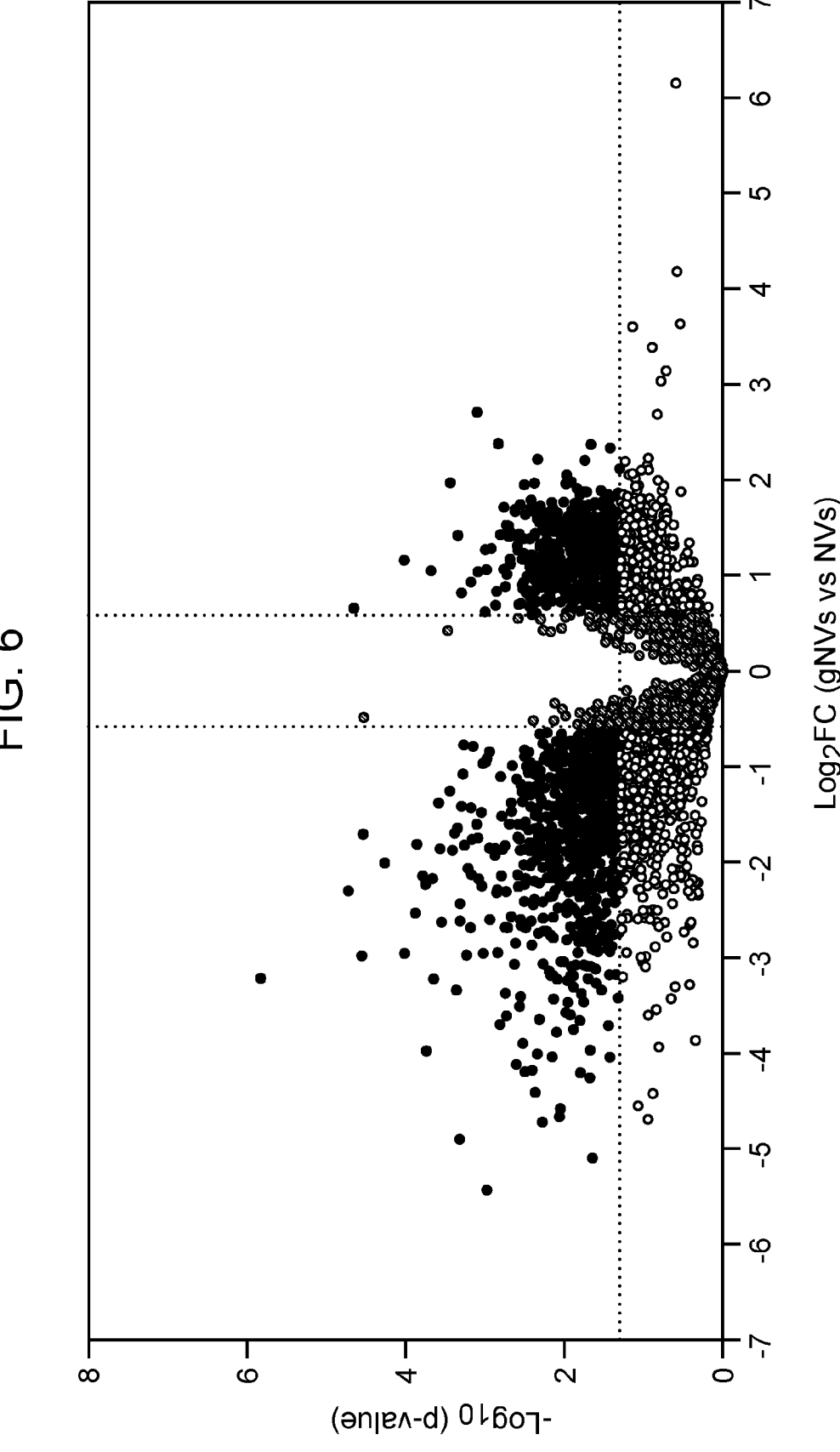
FIG. 6. depicts protein profile of NVs and gNVs. There are three groups based on 1.5 fold or higher change: 1) NV-enriched protein, 2) gNV-enriched protein; and 3) common protein.

Principal component analysis showed the first component separated 59% of the data based on vesicle type (gNVs and NVs) and the second component separated 18% of the data by replicate (FIG. 4A), indicating that gNV proteins are distinct from NV proteins. Hierarchical cluster analysis produced similar results, with samples clustering first as vesicle type (gNVs and NVs), and then by replicate (FIG. 4B), showing unique quantification profile of each group being closest together. And then, we identified 3536 and 3484 proteins from NVs and high pH-treated gNVs, respectively. As shown in the Venn diagram (FIG. 5A), 3483 proteins were identified in both vesicle preparations, whereas 53 and 1 proteins were uniquely identified in NVs and gNVs, respectively. The relative abundance of different proteins was obtained using the MaxQuant software and was plotted as shown in FIG. 5B. Based on the relative protein abundance, 2231 proteins did not change markedly in abundance among 3483 proteins. However, 515 and 737 proteins were relatively increased (1.5-fold) and decreased (1.5-fold)

in gNVs, respectively. Volcano plot of identified protein in NVs and gNVs revealed also similar patterns (FIG. 6), showing that protein expression is differentially changed by high pH treatment.

Figure 7:
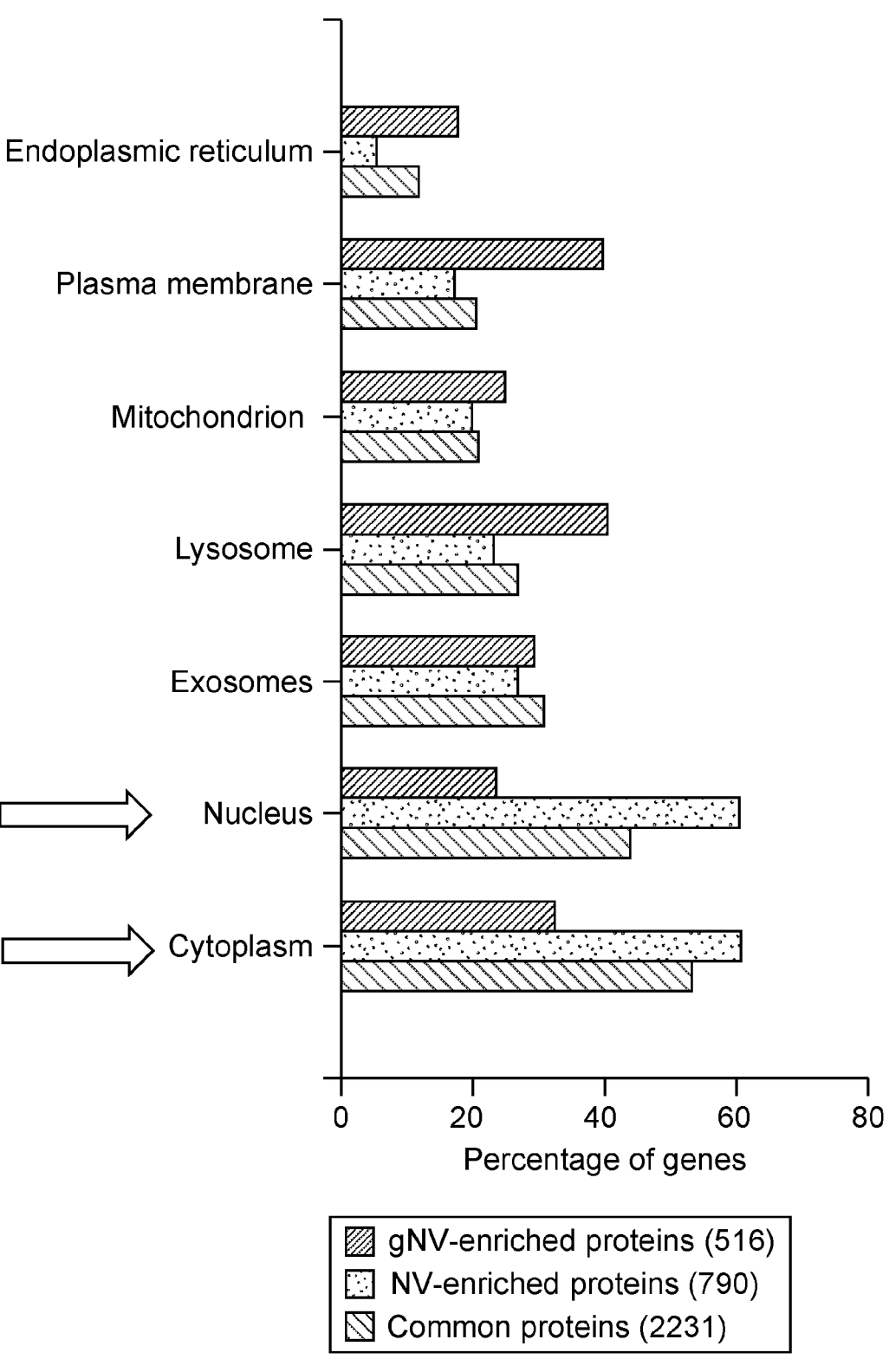
FIG. 7 illustrates that gNVs contain less nuclear and cytoplasmic proteins than NVs.
Figure 8:
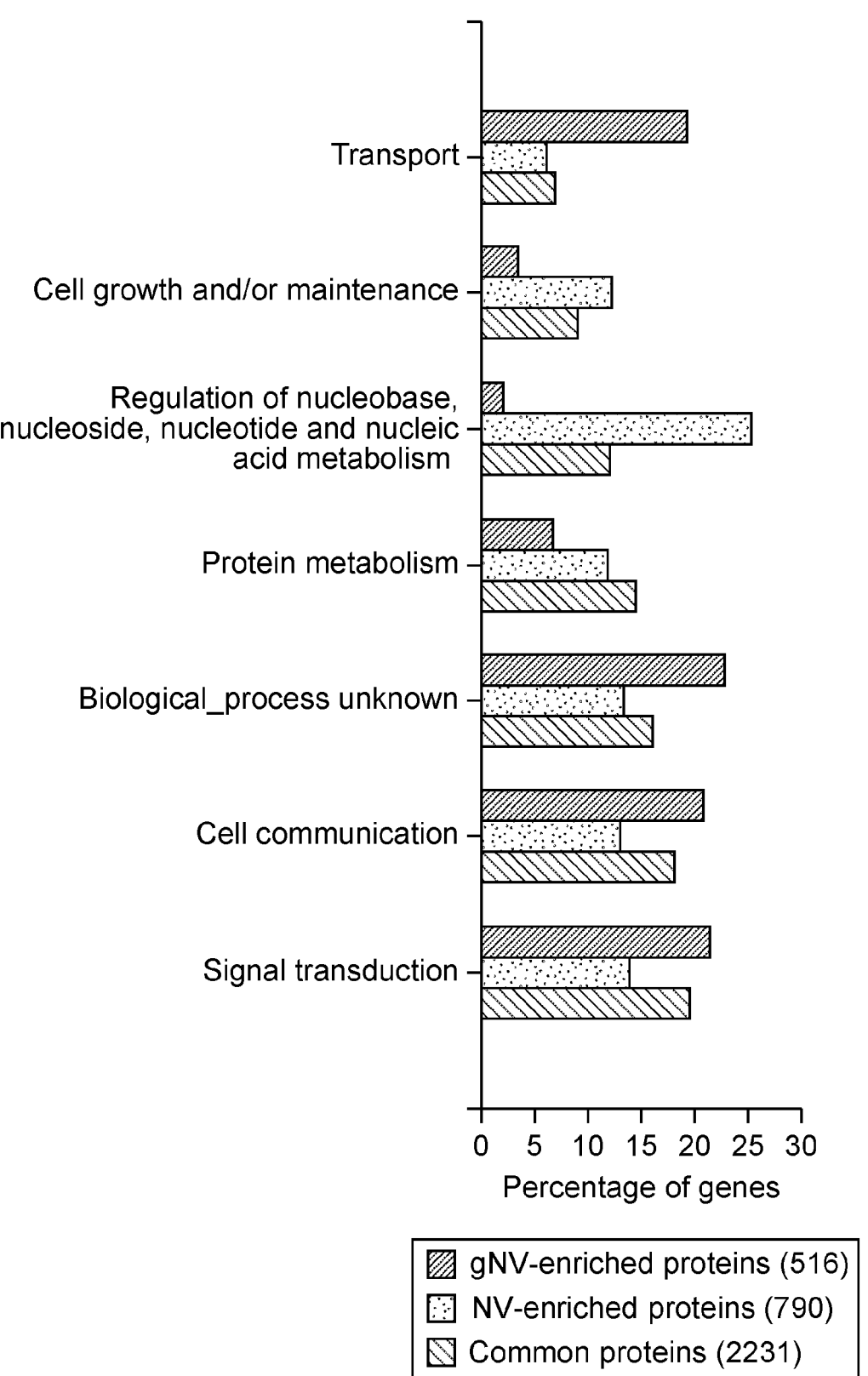
FIG. 8 illustrates that transport proteins is enriched in gNVs as compared to NVs and metabolic-pathway proteins are enriched in NVs.

In the GO term subcellular localization analysis, gNV-enriched proteome showed distinct feature from NV-enriched proteome (FIG. 7). gNV proteome was enriched with cell plasma membrane proteins, whereas NV proteome was enriched with cytosol and nucleus proteins. In the GO term biological process analysis, gNV proteome was enriched with biological processes including transport (FIG. 8). By contrast, NV proteome was enriched with biological processes including nucleic acid metabolism.

Example 3: gNVs Reduce OMV-Induced Inflammation

Methods

RAW 264.7 Cytokines

RAW 264.7 ($1×10^5$), a mouse macrophage cell line, were seeded into 24-well plates. OMVs were applied to the cells to induce pro-inflammatory cytokines (TNF-α and IL-6) for 3 h. NVs or gNVs were added for an additional 15 h. Supernatant concentrations of cytokines were measured by ELISA kit (R&D systems).

Mice Experiments

Mice (wild-type mice of the C57BL/6 genetic background, 6 weeks old) were intraperitoneally (i.p.) injected with OMVs (15 ug). Mice were intraperitoneally with NVs or gNVs and sacrificed at 6 h from OMV injection. Peritoneal fluid (PF) and blood were collected from mice, and then cytokines in the supernatant were analyzed by DuoSet ELISA Development kit (R&D Systems).

Figure 9:
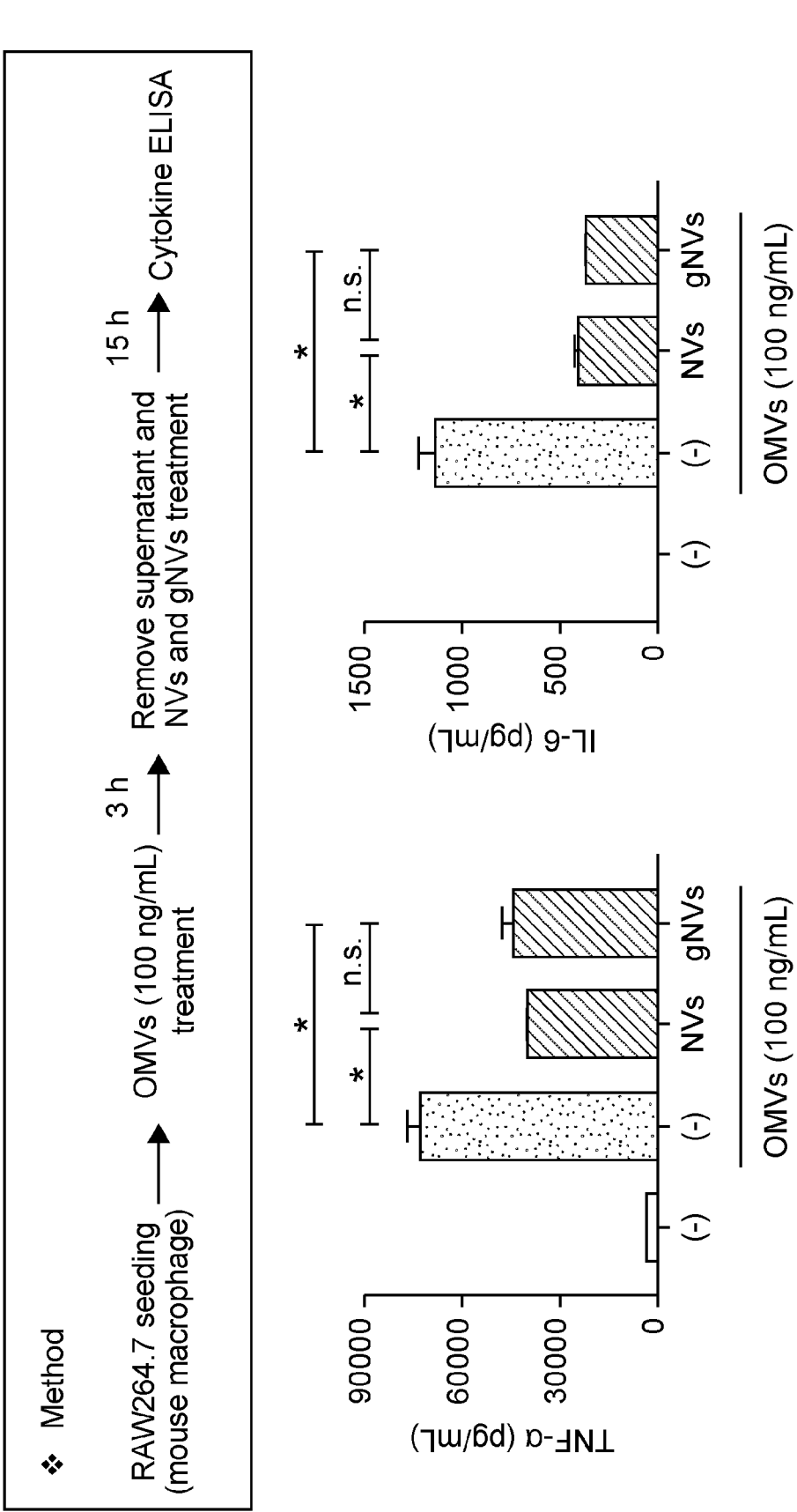
FIG. 9 illustrates that gNVs inhibit outer membrane vesicles-induced inflammatory response to an extent similar to NVs.
Figure 10:
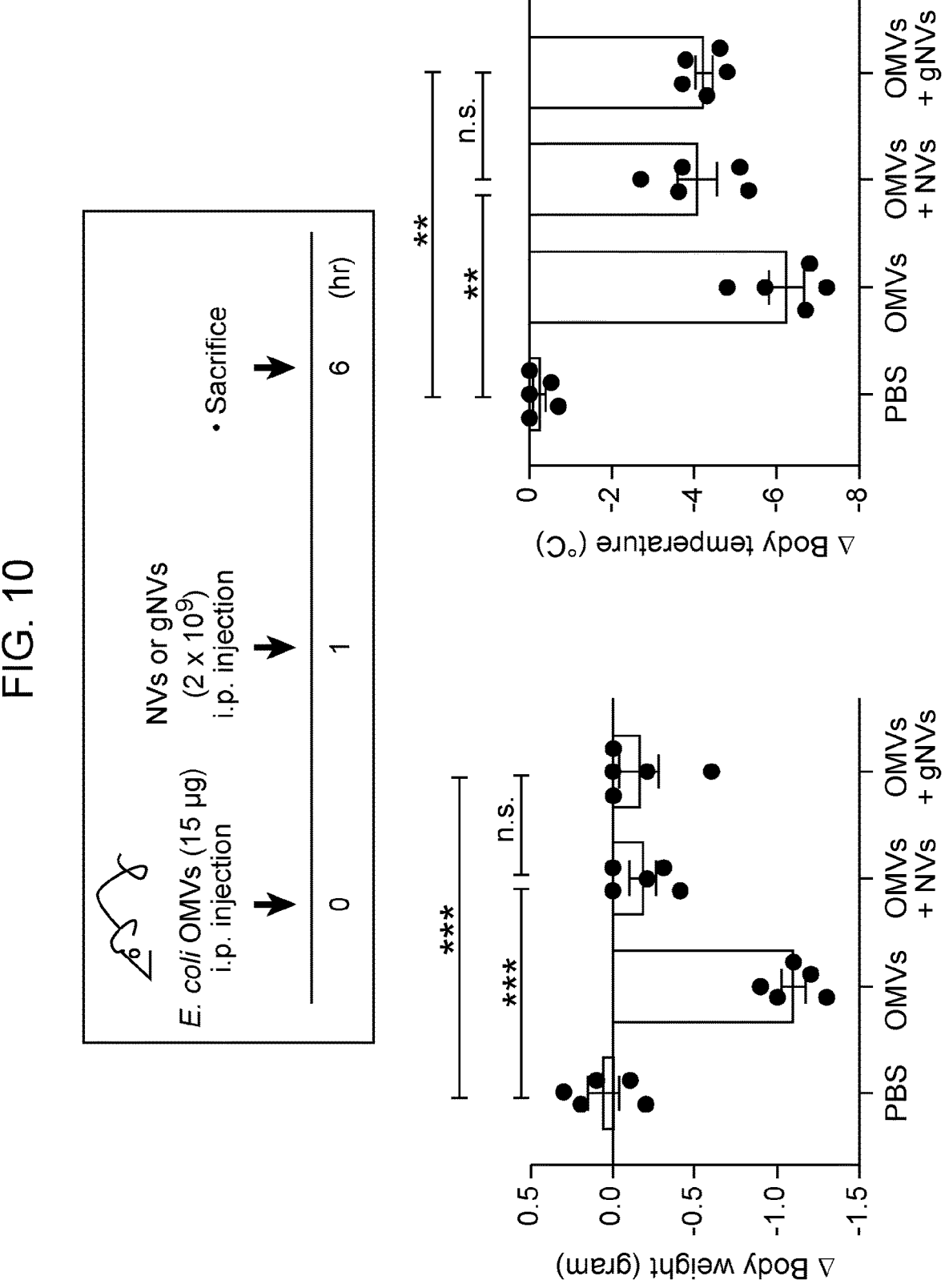
FIG. 10 illustrates that gNVs inhibit OMV-induced body weight and body temperature decrease in vivo, comparable to NVs.
Figures 11, 12:
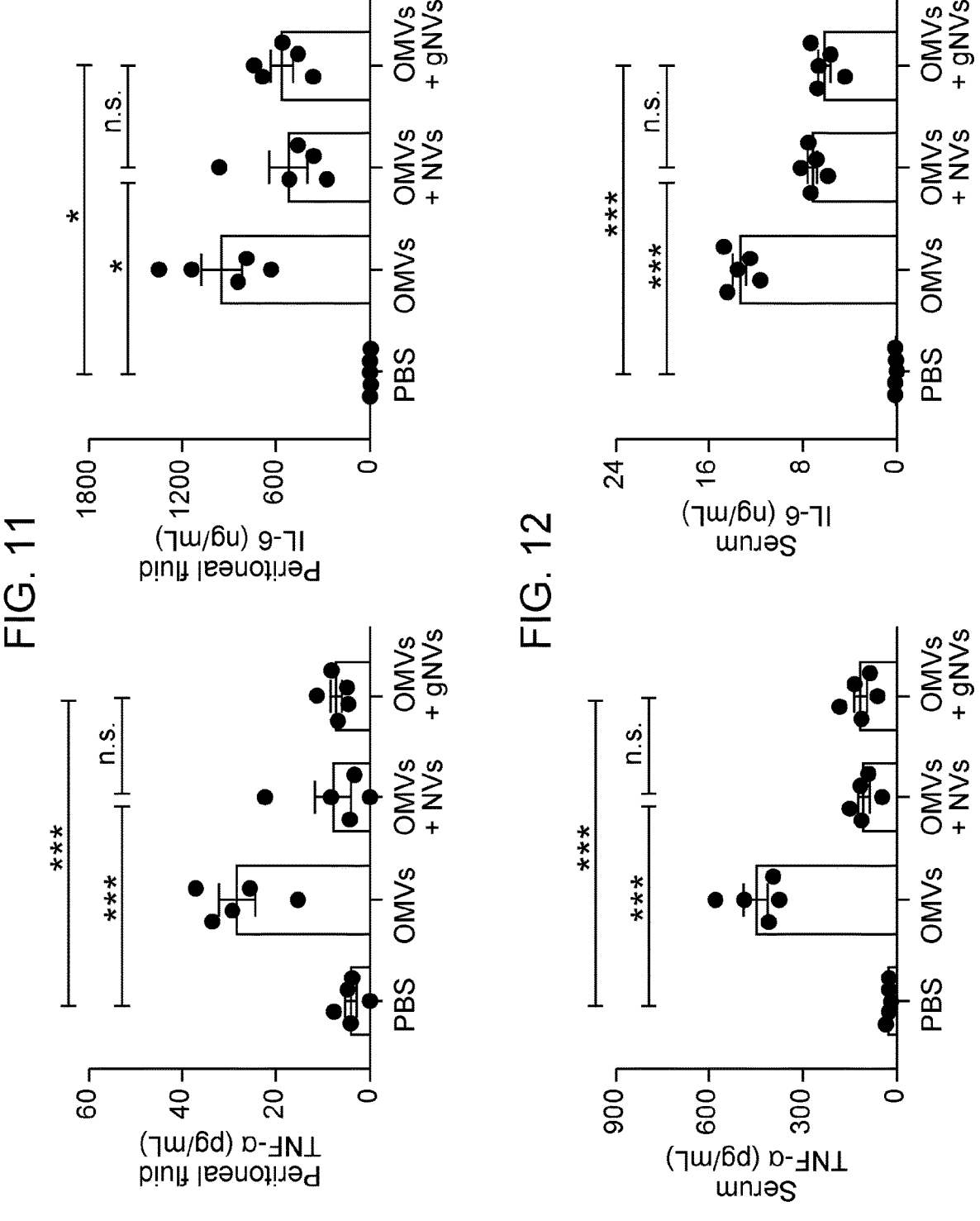
FIG. 11 illustrates that gNVs inhibit OMV-induced peritoneal inflammation in vivo, comparable to NVs.
FIG. 12 illustrates that gNVs inhibit OMV-induced systemic inflammation in vivo, comparable to NVs.

Bacterial OMVs have been considered as infectious agents to induce inflammation. rgNVs reduced significantly OMV-induced the release of TNF-α and IL-6 from RAW 264.7 cells comparable to NVs, revealing anti-inflammatory role of gNVs (FIG. 9). Also, a decreased pattern in body weight and temperature loss commonly observed after OMV-exposure, was recovered by gNVs at 6 hours (FIG. 10). Moreover, administration of gNVs significantly reduced the elevation of peritoneal fluid (FIG. 11) and serum cytokines (FIG. 12) by OMVs, suggesting the gNVs retain therapeutic potency after high pH treatment.

What is claimed is:

1. A method of making ghost nanovesicles (gNVs) deficient in cytoplasmic proteins and nucleic acids, the method comprising:
   disrupting mesenchymal stem cells (MSCs) to generate vesicles;
   separating the vesicles based on density and isolating nanovesicles;
   exposing the isolated nanovesicles to an alkaline pH to open the nanovesicles thereby generating plasma membrane sheets;
   purifying the plasma membrane sheets; and
   applying energy to the purified plasma membrane sheets sufficient to convert the plasma membrane sheets into gNVs.

2. The method of claim 1, wherein the gNVs are large gNVs having a diameter of 100 nm-200 nm, wherein the gNVs are small gNVs having a diameter of 40 nm-100 nm, or wherein the gNVs comprise large gNVs having a diameter of 100 nm-200 nm and small gNVs having a diameter of 40 nm-100 nm.

3. The method of claim 1, further comprising adding a therapeutic agent to a composition comprising the purified membrane sheets and applying energy to the composition sufficient to convert the plasma membrane sheets into gNVs comprising the therapeutic agent.

4. The method of claim 3, wherein the therapeutic agent comprises a small molecule, a peptide, a nucleic acid, or a polypeptide.

5. The method of claim 3, wherein the therapeutic agent is an anti-inflammatory agent.

6. The method of claim 4, wherein the therapeutic agent is not an anti-inflammatory agent.

7. The method of claim 1, wherein the MSCs are human MSCs.

8. Ghost nanovesicles (gNVs) derived from mesenchymal stem cells (MSCs), wherein the gNVs are deficient in cytoplasmic proteins and nucleic acids and are made by a method comprising:

disrupting the MSCs to generate vesicles;

separating the vesicles based on density and isolating nanovesicles;

exposing the isolated nanovesicles to an alkaline pH to open the nanovesicles thereby generating plasma membrane sheets;

purifying the plasma membrane sheets; and applying energy to the purified plasma membrane sheets sufficient to convert the plasma membrane sheets into gNVs.

9. The gNVs of claim 8, wherein the MSCs are human MSCs.

10. The gNVs of claim 8, comprising a therapeutic agent.

11. The gNVs of claim 10, wherein the therapeutic agent is an anti-inflammatory agent.

12. The gNVs of claim 10, wherein the therapeutic agent comprises a small molecule, a peptide, a nucleic acid, or a polypeptide and is not an anti-inflammatory agent.

13. A method for reducing level of a pro-inflammatory cytokine in a subject with an inflammatory related condition, the method comprising:

disrupting mesenchymal stem cells (MSCs) to generate vesicles;

separating the vesicles based on density and isolating nanovesicles;

exposing the isolated nanovesicles to an alkaline pH to open the nanovesicles thereby generating plasma membrane sheets;

purifying the plasma membrane sheets;

applying energy to the purified plasma membrane sheets sufficient to convert the plasma membrane sheets into ghost nanovesicles (gNVs);

administering to the subject an amount of the gNVs effective to reduce the level of the proinflammatory cytokine in the subject, wherein the pro-inflammatory cytokine comprises tumor necrosis factor alpha (TNF-$\alpha$) or interleukin-6 (IL-6).

14. The method of claim 13, wherein the subject is human and the MSCs are human MSCs.

15. The method of claim 13, wherein the pro-inflammatory cytokine is TNF-$\alpha$.

16. The method of claim 13, wherein the pro-inflammatory cytokine is IL-6.

\* \* \* \* \*